US010272141B2

(12) United States Patent
Fallon

(10) Patent No.: US 10,272,141 B2
(45) Date of Patent: Apr. 30, 2019

(54) PHARMACEUTICAL PREPARATION FOR THE TREATMENT OF THE SYMPTOMS OF ADDICTION AND METHOD OF DIAGNOSING SAME

(71) Applicant: Curemark, LLC, Rye, NY (US)

(72) Inventor: Joan M. Fallon, Bronxville, NY (US)

(73) Assignee: CUREMARK, LLC, Rye, NY (US)

( * ) Notice: Subject to any disclaimer, the term of this patent is extended or adjusted under 35 U.S.C. 154(b) by 0 days.

(21) Appl. No.: 15/593,121

(22) Filed: May 11, 2017

(65) Prior Publication Data

US 2018/0071374 A1 Mar. 15, 2018

Related U.S. Application Data

(63) Continuation of application No. 14/639,425, filed on Mar. 5, 2015, now Pat. No. 9,687,534, which is a continuation of application No. 13/926,822, filed on Jun. 25, 2013, now Pat. No. 9,017,665, which is a continuation of application No. 13/562,999, filed on Jul. 31, 2012, now Pat. No. 8,486,390, which is a continuation of application No. 13/271,783, filed on Oct. 12, 2011, now Pat. No. 8,318,158, which is a continuation of application No. 12/426,794, filed on Apr. 20, 2009, now Pat. No. 8,084,025.

(60) Provisional application No. 61/046,026, filed on Apr. 18, 2008.

(51) Int. Cl.
*A61K 38/54* (2006.01)
*A61K 38/47* (2006.01)
*A61K 38/46* (2006.01)
*A61K 38/48* (2006.01)

(52) U.S. Cl.
CPC ............ *A61K 38/54* (2013.01); *A61K 38/465* (2013.01); *A61K 38/47* (2013.01); *A61K 38/4826* (2013.01); *A61K 38/4873* (2013.01)

(58) Field of Classification Search
None
See application file for complete search history.

(56) References Cited

U.S. PATENT DOCUMENTS

| | | |
|---|---|---|
| 3,002,883 A | 10/1961 | Butt et al. |
| 3,223,594 A | 12/1965 | Hoek |
| 3,322,626 A | 5/1967 | D'Argento |
| 3,357,894 A | 12/1967 | Uriel et al. |
| 3,515,642 A | 6/1970 | Hiroyuki et al. |
| 3,574,819 A | 4/1971 | Franz et al. |
| 3,860,708 A | 1/1975 | Prout |
| 3,940,478 A | 2/1976 | Kurtz |
| 4,079,125 A | 3/1978 | Sipos |
| 4,145,410 A | 3/1979 | Sears |
| 4,241,046 A | 12/1980 | Papahadjopoulos et al. |
| 4,280,971 A | 7/1981 | Wischniewski et al. |
| 4,447,412 A | 5/1984 | Bilton |
| 4,456,544 A | 6/1984 | Lupova et al. |
| 4,500,515 A | 2/1985 | Libby |
| 4,623,624 A | 11/1986 | Schultze |
| 4,826,679 A | 5/1989 | Roy |
| 5,023,108 A | 6/1991 | Bagaria et al. |
| 5,190,775 A | 3/1993 | Klose |
| 5,227,166 A | 7/1993 | Ueda et al. |
| 5,250,418 A | 10/1993 | Moller et al. |
| 5,324,514 A | 6/1994 | Sipos |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,607,863 A | 3/1997 | Chandler |
| 5,648,335 A | 7/1997 | Lewis et al. |
| 5,674,532 A | 10/1997 | Atzl et al. |
| 5,686,311 A | 11/1997 | Shaw |
| 5,750,104 A | 5/1998 | Sipos |
| 5,753,223 A | 5/1998 | Shibahara et al. |

(Continued)

FOREIGN PATENT DOCUMENTS

| | | |
|---|---|---|
| CA | 2198317 A1 | 8/1998 |
| CA | 2263703 A1 | 8/1999 |

(Continued)

OTHER PUBLICATIONS

Hamel et al. Digestive Diseases (1978) 23(2): 264-268 (Year: 1978).*
Singh Int. J. Pancreatology (1987) 2: 311-324 (Year: 1987).*
Gass et al. Gastroenterology (2007) 133: 472-480 (Year: 2007).*
Ijuin et al. Kurume Med. J. (1998) 45: 1-5 (Year: 1998).*
Bouhnik, et al. Lactulose ingestion increases faecal bifidobacterial counts: A randomized double-blind study in healthy humans. European Journal of Clinical Nutrition 58:462-466 (2004).
Chaignon et al. Susceptibility of staphylococcal biofilms to enzymatic treatments depends on their chemical compositions. Appl. Microbiol. Appl. Microbiol. 75:125-132 (2007).

(Continued)

*Primary Examiner* — Susan M Hanley
(74) *Attorney, Agent, or Firm* — Wilson Sonsini Goodrich & Rosati

(57) ABSTRACT

A therapeutic agent for the treatment of the symptoms of addiction and the method for preparing the therapeutic agent is disclosed. The therapeutic agent is a stable pharmaceutical preparation containing, but not limited to, digestive/pancreatic enzymes. The therapeutic agent may be manufactured by a variety of encapsulation technologies. Delivery of the therapeutic agent may be made orally, through injection, by adherence of a medicated patch or other method. Further, a method of using of a biomarker, the presence of chymotrypsin in the gastrointestinal tract to determine the presence of symptoms of addiction, and the likelihood of relapsing into addiction is disclosed.

9 Claims, No Drawings

(56) References Cited

U.S. PATENT DOCUMENTS

| | | |
|---|---|---|
| 5,776,917 A | 7/1998 | Blank et al. |
| 5,858,758 A | 1/1999 | Hillman et al. |
| 5,952,178 A | 9/1999 | Lapidus et al. |
| 5,958,875 A | 9/1999 | Longo et al. |
| 5,977,175 A | 11/1999 | Lin |
| 5,985,891 A | 11/1999 | Rowe |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |
| 6,096,338 A | 8/2000 | Lacy et al. |
| 6,100,080 A | 8/2000 | Johansen |
| 6,149,585 A | 11/2000 | Gray |
| 6,153,236 A | 11/2000 | Wu et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,238,727 B1 | 5/2001 | Takemoto et al. |
| 6,251,478 B1 | 6/2001 | Pacifico et al. |
| 6,261,602 B1 | 7/2001 | Calanchi et al. |
| 6,261,613 B1 | 7/2001 | Narayanaswamy et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,632,429 B1 | 10/2003 | Fallon |
| 6,660,831 B2 | 12/2003 | Fallon |
| 6,699,885 B2 | 3/2004 | Phillips |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,890,561 B1 | 5/2005 | Blatt et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,211,661 B2 | 7/2012 | Fallon |
| 8,221,747 B2 | 7/2012 | Ortenzi et al. |
| 8,318,158 B2 | 11/2012 | Fallon |
| 8,437,689 B2 | 5/2013 | Mazar |
| 8,486,390 B2 | 7/2013 | Fallon |
| 8,580,522 B2 | 11/2013 | Fallon |
| 8,613,918 B2 | 12/2013 | Fallon |
| 8,658,163 B2 | 2/2014 | Fallon |
| 8,778,335 B2 | 7/2014 | Fallon |
| 8,815,233 B2 | 8/2014 | Fallon |
| 8,921,054 B2 | 12/2014 | Fallon |
| 8,980,252 B2 | 3/2015 | Fallon et al. |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 9,084,784 B2 | 7/2015 | Fallon et al. |
| 9,107,419 B2 | 8/2015 | Fallon et al. |
| 9,233,146 B2 | 1/2016 | Fallon |
| 9,320,780 B2 | 4/2016 | Fallon |
| 9,345,721 B2 | 5/2016 | Fallon et al. |
| 9,377,459 B2 | 6/2016 | Fallon |
| 9,408,895 B2 | 8/2016 | Fallon |
| 9,492,515 B2 | 11/2016 | Fallon et al. |
| 9,511,125 B2 | 12/2016 | Fallon et al. |
| 9,624,525 B2 | 4/2017 | Fallon |
| 9,624,526 B2 | 4/2017 | Fallon |
| 9,687,534 B2 * | 6/2017 | Fallon .................. A61K 38/47 |
| 2001/0006644 A1 | 7/2001 | Bova et al. |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0081628 A1 | 6/2002 | Fallon |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0258599 A1 | 11/2006 | Childers |
| 2006/0259995 A1 | 11/2006 | Cayouette et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |

(56) References Cited

U.S. PATENT DOCUMENTS

| | | |
|---|---|---|
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon et al. |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0187525 A1 | 8/2008 | Porubcan |
| 2008/0199448 A1 | 8/2008 | Ross et al. |
| 2008/0219966 A1 | 9/2008 | Fallon |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0063402 A1 | 3/2009 | Hayter |
| 2009/0110674 A1 | 4/2009 | Loizou |
| 2009/0117180 A1 | 5/2009 | Ortenzi et al. |
| 2009/0130081 A1 | 5/2009 | Fallon |
| 2009/0197289 A1 | 8/2009 | Fallon |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0285790 A1 | 11/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0065628 A1 | 3/2011 | Johnson et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon et al. |
| 2012/0027848 A1 | 2/2012 | Fallon et al. |
| 2012/0070504 A1 | 3/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2013/0059001 A1 | 3/2013 | Fallon |
| 2013/0095152 A1 | 4/2013 | Fallon |
| 2013/0113129 A1 | 5/2013 | Fallon et al. |
| 2013/0195833 A1 | 8/2013 | Fallon |
| 2013/0202581 A1 | 8/2013 | Fallon et al. |
| 2013/0224172 A1 | 8/2013 | Fallon et al. |
| 2013/0323223 A1 | 12/2013 | Fallon et al. |
| 2014/0030333 A1 | 1/2014 | Fallon |
| 2014/0127184 A1 | 5/2014 | Fallon et al. |
| 2014/0147500 A1 | 5/2014 | Fallon et al. |
| 2014/0161787 A1 | 6/2014 | Fallon |
| 2014/0170637 A1 | 6/2014 | Fallon |
| 2014/0348881 A1 | 11/2014 | Fallon |
| 2015/0023944 A1 | 1/2015 | Fallon |
| 2015/0147308 A1 | 5/2015 | Fallon et al. |
| 2015/0150955 A1 | 6/2015 | Fallon et al. |
| 2015/0151198 A1 | 6/2015 | Dugan et al. |
| 2015/0174219 A1 | 6/2015 | Fallon |
| 2015/0182607 A1 | 7/2015 | Jolly et al. |
| 2015/0246104 A1 | 9/2015 | Fallon et al. |
| 2015/0246105 A1 | 9/2015 | Fallon et al. |
| 2015/0273030 A1 | 10/2015 | Fallon |
| 2015/0335589 A1 | 11/2015 | Fallon et al. |
| 2016/0045576 A1 | 2/2016 | Fallon et al. |
| 2016/0206708 A1 | 7/2016 | Fallon et al. |
| 2016/0213697 A1 | 7/2016 | Fallon |
| 2016/0266113 A1 | 9/2016 | Fallon |
| 2016/0287683 A1 | 10/2016 | Fallon |
| 2018/0161409 A1 | 6/2018 | Fallon |

FOREIGN PATENT DOCUMENTS

| | | |
|---|---|---|
| CA | 2667976 A1 | 5/2008 |
| CN | 1031562 A | 3/1989 |
| CN | 1329923 A | 1/2002 |
| CN | 1552836 A | 12/2004 |
| DE | 3738599 A1 | 5/1989 |
| DE | 4332985 A1 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1413202 A1 | 4/2004 |
| EP | 1335706 B1 | 4/2005 |
| EP | 1019072 B1 | 5/2005 |
| EP | 1604677 A1 | 12/2005 |
| EP | 1931317 B1 | 12/2008 |
| EP | 2258837 A1 | 12/2010 |
| EP | 2318035 A1 | 5/2011 |
| EP | 2373791 A1 | 10/2011 |
| GB | 669782 A | 4/1952 |
| GB | 2347742 A | 9/2000 |
| GB | 2480772 A | 11/2011 |
| JP | S62230714 A | 10/1987 |
| JP | H04364119 A | 12/1992 |
| JP | 2003517831 A | 6/2003 |
| JP | 2005515223 A | 5/2005 |
| JP | 2006512091 A | 4/2006 |
| JP | 2007523664 A | 8/2007 |
| JP | 2008512468 A | 4/2008 |
| JP | 2008283895 A | 11/2008 |
| KR | 20050084485 A | 8/2005 |
| RU | 2356244 C1 | 5/2009 |
| TW | 310277 B | 7/1997 |
| WO | WO-8402846 A1 | 8/1984 |
| WO | WO-8908694 A1 | 9/1989 |
| WO | WO-9002562 A1 | 3/1990 |
| WO | WO-9419005 A1 | 9/1994 |
| WO | WO-9522344 A1 | 8/1995 |
| WO | WO-9732480 A1 | 9/1997 |
| WO | WO-9822499 A2 | 5/1998 |
| WO | WO-9826807 A1 | 6/1998 |
| WO | WO-9822499 A3 | 7/1998 |
| WO | WO-9832336 A2 | 7/1998 |
| WO | WO-9852593 A1 | 11/1998 |
| WO | WO-9964059 A2 | 12/1999 |
| WO | WO-0009142 A1 | 2/2000 |
| WO | WO-9964059 A3 | 3/2000 |
| WO | WO-0021504 A1 | 4/2000 |
| WO | WO-0127612 A2 | 4/2001 |
| WO | WO-0143764 A2 | 6/2001 |
| WO | WO-0145835 A1 | 6/2001 |
| WO | WO-0127612 A3 | 10/2001 |
| WO | WO-0143764 A3 | 11/2001 |
| WO | WO-0214537 A2 | 2/2002 |
| WO | WO-0219828 A1 | 3/2002 |
| WO | WO-0214537 A3 | 5/2002 |
| WO | WO-02051352 A2 | 7/2002 |
| WO | WO-02051436 A2 | 7/2002 |

(56) References Cited

FOREIGN PATENT DOCUMENTS

| | | |
|---|---|---|
| WO | WO-03051345 A2 | 6/2003 |
| WO | WO-03059088 A1 | 7/2003 |
| WO | WO-2004060074 A1 | 7/2004 |
| WO | WO-2004093883 A2 | 11/2004 |
| WO | WO-2005115445 A1 | 12/2005 |
| WO | WO-2006031554 A2 | 3/2006 |
| WO | WO-2006044529 A1 | 4/2006 |
| WO | WO-2006031554 A3 | 9/2006 |
| WO | WO-2007002572 A2 | 1/2007 |
| WO | WO-2007074454 A2 | 7/2007 |
| WO | WO-2007147714 A1 | 12/2007 |
| WO | WO-2008021987 A2 | 2/2008 |
| WO | WO-2008102264 A2 | 8/2008 |
| WO | WO-2009114757 A2 | 9/2009 |
| WO | WO-2009155689 A1 | 12/2009 |
| WO | WO-2010002972 A1 | 1/2010 |
| WO | WO-2010025126 A1 | 3/2010 |
| WO | WO-2010080830 A1 | 7/2010 |
| WO | WO-2010080835 A1 | 7/2010 |
| WO | WO-2010120781 A1 | 10/2010 |
| WO | WO-2011000924 A1 | 1/2011 |
| WO | WO-2011114225 A1 | 9/2011 |

OTHER PUBLICATIONS

Co-pending U.S. Appl. No. 15/593,124, filed May 11, 2017.
Co-pending U.S. Appl. No. 15/593,129, filed May 11, 2017.
Kidd, P.M., Autism, an extreme challenge to integrative medicine. Part 2: medical management. Altern. Med. Rev., 7(6):172-499 (Dec. 2002).
Marion et al., A New Procedure Allowing the Complete Removal and Prevention of Hemodialysis. Blood Purification, 23:339-348 (2005).
Neumeyer, Ann. M. et al. Brief Report: Bone Fractures in Children and Adults with Autism Spectrum Disorders. J. Autism Dev. Disord. 45(3):881-887 (Mar. 2016).
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
P.Ya. Grigoryev et al., Reference Guide on Gastroenterology, Moscow, MIA-2003, pp. 454,460,465.
Tuohy, K.M. et al. Using probiotics and prebiotics to improve gut health. Reviews, Therapeutic Focus, DDT 8(15) Aug. 2003.
U.S. Appl. No. 12/054,343 Final Office Action dated May 10, 2017.
U.S. Appl. No. 12/786,739 Final Office Action dated Jun. 23, 2017.
U.S. Appl. No. 13/503,844 Final Office Action dated Nov. 30, 2017.
U.S. Appl. No. 13/733,873 Non-Final Office Action dated May 25, 2017.
U.S. Appl. No. 13/757,412 Final Office Action dated Sep. 12, 2017.
U.S. Appl. No. 13/836,135 Final Office Action dated May 15, 2017.
U.S. Appl. No. 14/296,091 Final Office Action dated Aug. 23, 2017.
U.S. Appl. No. 14/612,580 Final Office Action dated Aug. 10, 2017.
U.S. Appl. No. 14/693,711 Notice of Allowability dated May 26, 2017.
U.S. Appl. No. 4 Notice of Allowance dated Oct. 19, 2017.
U.S. Appl. No. 14/713,242 Final Office Action dated Jul. 21, 2017.
U.S. Appl. No. 15/089,842 Office Action dated Dec. 8, 2017.
U.S. Appl. No. 15/185,511 Notice of Allowance dated Nov. 16, 2017.
ABCnews. Changing Face of Autism: Numbers Rise as More Behaviors Included. ABCnews. Nov. 1, 2007.
Adams. Summary of Defeat Autism Now! (DNN!) Oct. 2001 Conference, retrieved from the internet Dec. 18, 2008. http://puterakembara.org/rm/DAN2001.htm.
Advisory Action dated Jun. 3, 2008 for U.S. Appl. No. 10/681,018.
Aman, et al. Outcome measures for clinical drug trials in autism. CNS Spectr. Jan. 2004;9(1):36-47.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Ang, et al. Biological role and regulation of the universally conserved heat shock proteins. J Biol Chem. Dec. 25, 1991;266(36):24233-6.
Anonymous: Emulsifiers for the preparation of active dry yeast, Research Disclosure, Mason Publications, Hampshire, GB, 236(6), Dec. 1983 (attached).
APDA. Basic Information About Parkinson's Disease. Jul. 14, 2008.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.

(56) References Cited

OTHER PUBLICATIONS

ASH. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
AUSTIC. Development and adaptation of protein digestion. J Nutr. May 1985;115(5):686-97.
Autism Diagnosis. Autism Statistics. Www.autism-diagnosis.com/autism_statistics/autism_statistics.html. 2007.
Autism Society of America. Incidence Numbers from Other Countries. www.autism-society.org. Accessed: Jul. 14, 2008.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. Correlation between protein intake and daily levodopa dosage, Obtained from the internet May 2, 2007, http://www.azilect.eu/media/cnsnews/showitem.aspx?i=d1c603e4-3c61-4aa1-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008; 12(6):476-9.
Barlow. A comparison of the blood pressure, kidney volume and the pancreatic secretory response following the vein administration of various secretin preparations. Am J Phys. 1927;81:182-188.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.
Belmonte et al. Fragile X syndrome and autism at the intersection of genetic and neural networks. Nat Neurosci. Oct. 2006; 9(10):1221-5 (abstract only).
Berg, et al. Section 10.5 Many Enzymes Are Actived by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.
Birnbaum, et al. Heat shock or stress proteins and their role as autoantigens in multiple sclerosis. Ann N Y Acad Sci. Dec. 19, 1997;835:157-67. Abstract only.
Blackmer. Parkinson disease: treatment and medication. Mar. 10, 2009., retrieved from the internet on Sep. 15, 2009, http://emedicine.medscape.com/article/312519-treatment.
Block, et al. A rapid food screener to assess fat and fruit and vegetable intake. Am J Prev Med. May 2000;18(4):284-8.
BLOG. Acid Phosphatase Research (blog). Acid-phosphatase.blogspot.com. 2008.
Bode et al. Usefulness of a simple photometric determination of chymotrypsin activity in stools—results of a multicentre study. Clin Biochem. 1986; 19:333-37.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Borowitz et al., Study of a novel pancreatic enzyme replacement therapy in pancreatic insufficient subjects with cystic fibrosis J.Pediatr., 149:658-662 (2006).
Borowitz, et al. Use of pancreatic enzyme supplements for patients with cystic fibrosis in the context of fibrosing colonopathy. Consensus Committee. J Pediatr. Nov. 1995;127(5):681-4.
Bowen. Exocrine secretions of the pancreas. Jul. 5, 2006. Accessed online at www.vivo.colostate.edu/hbooks/pathphys/digestion/pancreas/exocrine.html.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Bray, et al. Effect of dietary protein content on weight gain, energy expenditure, and body composition during overeating. A randomized controlled trial. JAMA. Jan. 4, 2012; 307(1):47-55.
Brinkley, et al. Factor analysis of the aberrant behavior checklist in individuals with autism spectrum disorders. J Autism Dev Disord. Nov. 2007;37(10):1949-59. Epub Dec. 21, 2006.
Brown. Background to Parkinson's Disease. biomed.brown.edu. Jul. 14, 2008.
Brudnak et al. Enzyme-based therapy for autism spectrum disorders—is it worth another look? Med Hypoth. 2002; 58:422-428.
Brudnak, Mark et al., Guide to intestinal health in autism spectrum disorder, Kirkman Laboratories, (Oct. 2001).
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Buie, et al. Evaluation, diagnosis, and treatment of gastrointestinal disorders in individuals with ASDs: a consensus report. Pediatrics. Jan. 2010;125 Suppl 1:S1-18.
Button, KS et al. Power failure: why small sample size undermines the reliability of neuroscience. Nat. Rev. Neurosci. 14:365376 (2013).
Calderon-Garciduenas, et al. Immunotoxicity and environment: immunodysregulation and systemic inflammation in children. Toxicol Pathol. 2009;37(2):161-9.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Campbell et al. A genetic variant that disrupts MET transcription is associated with autism. Proc Natl Acad Sci USA. 2006; 103(45):16834-16839.
Campbell, et al. Distinct genetic risk based on association of MET in families with co-occurring autism and gastrointestinal conditions. Pediatrics. Mar. 2009;123(3):1018-24.
Carlton. Autism and malnutrition: the milk connection. Retrieved from the internet on Feb. 18, 2008, http://www.mercola.com/2004/autism_malnutrition.htm.
Caronna, et al. Autism spectrum disorders: clinical and research frontiers. Arch Dis Child. Jun. 2008;93(6):518-23.
Carroccio, et al. Pancreatic enzyme therapy in childhood celiac disease. A double-blind prospective randomized study. Dig Dis Sci. Dec. 1995;40(12):2555-60.
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.

(56) References Cited

OTHER PUBLICATIONS

Cassidy, et al. A new concept for the mechanism of action of chymotrypsin: the role of the low-barrier hydrogen bond. Biochemistry. Apr. 15, 1997;36(15):4576-84.
CDC. Attention-Deficit/Hyperactivity Disorder (ADHD). Www.cdc.org. 2005.
CDC. Autism Information Center/FAQs. Dept of Health and Human Services/CDC. Jan. 30, 2008.
CDC, Escherichia coli, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
CDC. High Blood Pressure. Division for Heart Disease Stroke Prevention. Jul. 15, 2003.
Chazalette, J.P. et al., A double-bind placebo-controlled trial of a pancreatic enzyme formulation (Panzytrat 25000) in the treatment of impaired lipid digestion in patients with cystic fibrosis. Drug Invest., 5(5):274-280 (1993).
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Childhood Autism Rating Scale (CARS), Wikipedia, downloaded May 5, 2014.
Chung, et al. Effects of a central cholinesterase inhibitor on reducing falls in Parkinson disease. Neurology. Oct. 5, 2010;75(14):1263-9. Epub Sep. 1, 2010.
Cichoke, AJ the Complete Book of Enzyme Therapy, Penguin (1999) pp. 206-208 and 38.
Cichoke. Celiac disease. The complete book of enzyme therapy. Penguin. New York, NY. 1999; 174-177.
Cichoke, et al. The complete book of enzyme therapy. Penguin. 1998: 39, 42, 47, 50, and 53.
Cichoke. Influenza. In: The Complete Book of Enzyme Therapy. D. Stewart, ed. Copyright 1999. Anthony J. Cichoke. Penguin Putnam, Inc., New York, New York. pp. Contents, 50, 273-275 and 455.
Claud, et a. Hypothesis: inappropriate colonization of the premature intestine can cause neonatal necrotizing enterocolitis. FASEB J. Jun. 2001;15(8):1398-403.
Commentary on the Japanese Pharmacopoeia, 14th ed., D929-D931, 2001.
Concerta. ADHD Myths and Facts. ADHD Myths and Facts about medication, girls, and symptoms and causes. Concerta.net. Jul. 15, 2008.
Co-pending U.S. Appl. No. 15/265,415, filed Sep. 14, 2016.
Co-pending U.S. Appl. No. 15/265,620, filed Sep. 14, 2016.
Co-pending U.S. Appl. No. 15/354,940, filed Nov. 17, 2016.
Co-pending U.S. Appl. No. 15/440,942, filed Feb. 23, 2017.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
CREON—FDA Prescribing information side effects and uses. Revised Apr. 2015.
Creon digestive enzymes. Celic.com/ Jun. 2009. http://www.celiac.com/gluten-free/topic/59195-creon-digestive-enzymes.
CREON. Full prescribing information. Last edited Mar. 2013. Abbvie Inc 2012. www.rxabbvie.com/pdf/creon_Pl.pdf.
Croonenberghs, et al. Peripheral markers of serotonergic and noradrenergic function in post-pubertal, caucasian males with autistic disorder. Neuropsychopharmacology. Mar. 2000;22(3):275-83.
Cruse et al. Illustrated dictionary of immunology. CRC Press, New York. 1995.
Cuervo, et al. Cathepsin A regulates chaperone-mediated autophagy through cleavage of the lysosomal receptor. EMBO J. Jan. 2, 2003;22(1):47-59.
Curemark press release. Curemark Receives Investigational New Drug Clearance for CM-AT for Autism. Mar. 26, 2009. http://www.medicalnewstoday.com/releases/143723.php.
Curemark Trademark/Service mark application, Principal Register. Serial No. 77527223. Filing date: Jul. 21, 2008.
Dajcs, et al. Lysostaphin is effective in treating methicillin-resistant Staphylococcus aureus endophthalmitis in the rabbit. Curr Eye Res. Jun. 2001;22(6):451-7.
Darman. An introduction to alternative medicine for psychiactric conditions. Oct. 22, 2007, retrieved on Sep. 18, 2009, http://web.archive.org/web/20071022104238/http://altp[therapies4bipolar.info/ortho/html.
Dawe, et al. Antipsychotic drugs dose-dependently suppress the spontaneous hyperactivity of the chakragati mouse. Neuroscience. Nov. 24, 2010;171(1):162-72. Epub Sep. 17, 2010.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
Derwent. English abstract for RU 2286785 Nov. 10, 2006. Downloaded from the Derwent file Jul. 13, 2011.
Diaz-Hernandez, et al. Neuronal induction of the immunoproteasome in Huntington's disease. J Neurosci. Dec. 17, 2003;23(37):11653-61.
Digestive Enzyme Preparation: Pancreatin listed in Japanese Pharmacopoeia, Aug. 2008,<URL:http>(in Japanese with English translation)</URL:http:>.
Digestive Enzyme Wikipedia. Retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between helicobacter pylori infection and idiopathic parkinsonism. Medical Hypothsis. 2000; 55(2):93-98.
Dockter et al. Determination of chymotrypsin in the feces by a new photometric method. Padiatr Padol. 1985; 20(3):257-265.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Dupiereux, et al. Creutzfeldt-jakob, Parkinson, lewy body dementia and Alzheimer diseases: from diagnosis to therapy. Cent Nery Syst Agents Med Chem. Mar. 2009;9(1):2-11.
Durkin, et al. Socioeconomic inequality in the prevalence of autism spectrum disorder: evidence from a U.S. cross-sectional study. PLoS One. Jul. 12, 2010;5(7):e11551.
Eaves, et al. The criterion-related validity of the Childhood Autism Rating Scale and the Autism Behavior Checklist. J Abnorm Child Psychol. Oct. 1993;21(5):481-91. abstract only.
Edelson, et al. 3-Cyclohexene-1-glycine, an Isoleucine Antagonist. J. Am. Chem. Soc. 1958; 80(11):2698-2700.
Elkashef, et al. Biological markers of cocaine addiction: implications for medications development. Addict Biol. Jun. 2003;8(2):123-39.
Elphick, et al. Impaired luminal processing of human defensin-5 in Crohn's disease: persistence in a complex with chymotrypsinogen and trypsin. Am J Pathol. Mar. 2008;172(3):702-13.
Emc, Creon 10000 Capsules, May 18, 2015, Available Online at: www.medicines.org/uk/emc/medicine/2068.

(56) References Cited

OTHER PUBLICATIONS

EMedExpert, Antibiotics:Cephalosporins, Available online at: www.emedexpert.com/compare/cephalosporins.shtml, available as early as Jun. 2, 2007 per Internet Archive Wayback Machine.
Ethridge, et al. Acute pancreatitis results in induction of heat shock proteins 70 and 27 and heat shock factor-1. Pancreas. Oct. 2000;21(3):248-56.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
Exocrine Pancreatic Insufficiency (Enzymes) Document downloaded online on Jan. 8, 2016 at: http://www.epi4dogs.com/enzyme.htm< http:></http:>.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Fallon. Could one of the most widely prescribed antibiotics amoxicillin/clavulanate augmentin be a risk factor for autism? Med Hypotheses. 2005;64(2):312-5.
Family Caregiver Alliance. Fact Sheet: Parkinson's Disease. Caregiver.org. Jul. 14, 2008.
Fernell, et al. No evidence for a clear link between active intestinal inflammation and autism based on analyses of faecal calprotectin and rectal nitric oxide. Acta Paediatr. Jul. 2007;96(7):1076-9.
Ferrone, et al. Pancreatic enzyme pharmacotherapy. Pharmacotherapy. 2007; 27:910-920.
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb/ 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Fitzsimmons, et al. High-dose pancreatic-enzyme supplements and fibrosing colonopathy in children with cystic fibrosis. N Engl J Med. May 1, 1997;336(18):1283-9.
Fliri, et al. Drug effects viewed from a signal transduction network perspective. J Med Chem. Dec. 24, 2009;52(24):8038-46. doi: 10.1021/jm901001p.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of giardia lamblia, entamoeba histolytica/entamoeba dispar, and cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
Giglio, et al. Failure to thrive: the earliest feature of cystic fibrosis in infants diagnosed by neonatal screening. Acta Paediatr. Nov. 1997;86(11):1162-5.
GM Chemie 2010 Products: Hypromellose Phthalate accessed from www.gmchemie.com on Sep. 22, 2014.
Goff, et al. Production of abnormal proteins in *E. coli* stimulates transcription of Ion and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Analysis of data gaps pertaining to enterotoxigenic *Escherichia coli* in low and medium human development index countries, 1984-2005. Epidemiol Infect. 2008; 136:721-738.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. 1996 Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
Health.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Hendren et al. Mechanistic biomarkers for autism treatment. Medical Hypotheses. 2009; 73:950-954.
HITTI. Allergy, celiac disease, and ileal lymphonodular. WebMD. 2005. 1-2.
Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.
Holten, et al. Appropriate prescribing of oral beta-lactam antibiotics. Am Fam Physician. Aug. 1, 2000;62(3):611-20.
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Horvath et al. Improved social and language skills after secretin administration in patients with autistic spectrum disorders. Journal of the Association for Academic Minority Physicians. Jan. 1998; 9(1):9-15.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.

(56) References Cited

OTHER PUBLICATIONS

Huang, et al. Mapping of the human APOB gene to chromosome 2p and demonstration of a two-allele restriction fragment length polymorphism. Proc Natl Acad Sci U S A. Feb. 1986;83(3):644-8.
Information of Papain from Worthington Enzymes webpage http://www.worthington-biochem.com/pap/default.html Downloaded Jan. 17, 2013.
International preliminary report on patentability dated Jul. 17, 2014 for PCT/US2013/020183.
International search report and written opinion dated Feb. 21, 2013 for PCT/US2013/020183.
International search report and written opinion dated May 9, 2013 for PCT/US2013/024453.
International search report and written opinion dated Aug. 27, 2013 for PCT/US2013/043444.
International search report and written opinion dated Nov. 12, 2012 for PCT/US2012/034489.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al. Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Jenkins, et al. Management of gastroenteritis. Archives of Disease in Childhood. 1990; 65:939-941.
JUHL. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003;92(7):1489-501.
Kaemmerer, et al. Effects of lipid peroxidation-related protein modifications on RPE lysosomal functions and POS phagocytosis. Invest Ophthalmol Vis Sci. Mar. 2007;48(3):1342-7.
Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984; 30(11):1753-1757.
Katritos. New finding may have implications for schizophrenia, autism. Autism/Schizophrenia findings relating to protein, etc. Feb. 10, 2011. e-mail.

Kearney, et al. Global burden of hypertension: analysis of worldwide data. Lancet. Jan. 15-21, 2005;365(9455):217-23. Abstract only.
King, et al. Effects of bacterial microflora of the lower digestive tract of free-range waterfowl on influenza virus activation. Appl Environ Microbiol. Jun. 2011;77(12):4119-25. doi:10.1128/AEM.02578-10. Epub Apr. 29, 2011.
Knivsberg, et al. A randomised, controlled study of dietary intervention in autistic syndromes. Nutr Neurosci. Sep. 2002;5(4):251-61.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.
Koster et al. Evidence based medicine and extradigestive manifestations of helocobacter pylori. Acta Gastro-Enterologica Belgica. 2000; 63(4):388-392.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Kronenberg,et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Kumar. Neurologic presentations of nutritional deficiencies. Neurol Clin. Feb. 2010;28(1):107-70.
Larimore. How Common Is ADHD? Facts About ADHD. Jul. 15, 2008.
Lashkari, et al. Williams-Beuren syndrome: An update and review for the primary physician. Clinical Pediatrics. 1999; 38(4):189-208.
Layer et al. Pancreatic enzyme replacement therapy. Current Gastroenterology Reports. 2001; 3:101-108.
Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007;25(3):265-71.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Life Plus Somazyne accessed Jun. 10, 2016, Online at www.lifeplus.com/media/pdf/piSheets/US/ 6141-PI_EN.pdf.
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2)1 89-200.
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders. info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacDonald. Thyrotoxicosis treated with pancreatic extract and iodine. Lancet. 1943; 244(6251):788.

(56) References Cited

OTHER PUBLICATIONS

MacFabe, et al. Neurobiological effects of intraventricular propionic acid in rats: possible role of short chain fatty acids on the pathogenesis and characteristics of autism spectrum disorders. Behav Brain Res. 2006;176(1):149-69.
MacReady. Parkinson's Diseasne Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.
Marcus, et al. A placebo-controlled, fixed-dose study of aripiprazole in children and adolescents with irritability associated with autistic disorder. J Am Acad Child Adolesc Psychiatry. Nov. 2009;48(11):1110-19.
Marczewska et al. Protein intake in parkinsonian using the EPIC food frequency questionnaire. Mov Diord. Aug. 2006; 21(8):1229-1231.
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Matikainen, et al. Autonomic dysfunction in long-standing alcoholism. Alcohol Alcohol. 1986;21(1):69-73. Abstract only.
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/Dsection=symptoms.
McAlonan, et al. Brain anatomy and sensorimotor gating in Asperger's syndrome. ain. Jul. 2002;125(Pt 7):1594-606.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
MEDSAFE. Data sheet for alpha-lactose, Jul. 21, 2008, http://www.medsafe.govt.nz/Profs/Datasheet/a/Alphalactulosesyrup.htm.
MEDSCAPE. Burden of Hypertension in the United States Greater Than Ever. www.medscape.com. Jul. 14, 2004.
Melmed, et al. Metabolic markers and gastrointestinal symptoms in children with autism and related disorders. J Pediatr Gast Nutr. 2000; 31:S31-S32. Abstract only.
Merck. Autism, Merck manual online medical library home addition, retrieved from the internet Mar. 10, 2008, http://www.mercl.com/mmhge/sec23/ch286/ch286b.html.
Merriam-Webster 2014 Definition: Precipitate accessed from www.mirriam-webster.com on Sep. 22, 2014.
MeSH browser. Child Development Disorders, Pervasive, and Attention Deficit and Disruptive Behavior Disorders, National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michael's Naturopathic Programs, Digestive Enzymes, Product #011161, Accessed on Jun. 10, 2016, online at: www.michaelshealth.com/retail/digestive-enzymes-659.html.
Michell et al. Biomarkers and parkinson's disease. Brain. 2004; 127(8):1693-1705.
Millipore EMD catalog (online). Papain, unit definition, EMD Millipore Corp, 2013. Downloaded May 13, 2013.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mitsui, et al. Role of aminopepridases in the blood pressure regulation. Biological and Pharmaceutical Bulletin of Japan, Pharmaceutical Sociey of Japan. 2004; 27(6):768-771.
Mizutani, et al. Effects of placental proteases on maternal and fetal blood pressure in normal pregnancy and preeclampsia. Am J Hypertens. Jun. 1996;9(6):591-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Moretti, et al. Acute pancreatitis: hypertonic saline increases heat shock proteins 70 and 90 and reduces neutrophil infiltration in lung injury. Pancreas. Jul. 2009;38(5):507-14. Abstract only.
Mosqueira, et al. Chronic hypoxia impairs muscle function in the *Drosophila* model of Duchenne's muscular dystrophy (DMD). PLoS One. Oct. 20, 2010;5(10):e13450.
Munasinghe et al. Digestive enzyme supplementation for autism spectrum disorders: a double-blind randomized controlled trial. J Autism Dev Disord. Sep. 2010;40(9):1131-8.
Munasinghe et al. Digestive enzyme supplementation for autism spectrum disorders: a double-blind randomized controlled trial. J Autism Dev Disord. Sep. 2010;40(9):1131-8. Abstract only.
Nachaegari et al. Coprocessed excipients for solid dosage forms. Pharmaceutical Technology. 2004; p. 52, 54, 56 ,58, 60, 64.
Nagamoto. Jacobson: Psychiatric Secrets, 2nd ed. 2001. Ch 28 Antipsychotic meds.
Neuer, et al. The role of heat shock proteins in reproduction. Hum Reprod Update. Mar.-Apr. 2000;6(2):149-59.
Nevo et al. Acute immune polyneuropathies: correlations of serum antibodies to campylobacter jejuni and helicobacter pylori with anti-gm antibodies and clinical patterns of disease. J of Inf diseases. 1997; 175(S2):S154-6.
Newhorizons. ADD/ADHD: New Perspectives on Attentional Priority Disorders. New Horizons for Learning. Jul. 15, 2008.
NIH, Celiac Disease, National Digestive Diseases Information Clearinghouse: Bethesda, MD, 2008; 12 pages.
NIH. National Institutes of Health. National Diabetes Statistics 2007. diabetes.niddk.nih.gov. Jun. 1, 2008.
NINDS Dysautonimia Information Page, retrieved from the internet Sep. 10, 2009, http://www.ninds.nih.gov/disorders/dysautonomia/dysautonomia.htm.
NINDS Guillain-Barre Syndrome Information Page, retrieved from the internet Sep. 15, 2009, http://www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of allowance dated Jan. 2, 2014 for U.S. Appl. No. 13/204,881.
Notice of allowance dated Feb. 2, 2015 for U.S. Appl. No. 13/926,822.
Notice of Allowance dated Feb. 17, 2012 for U.S. Appl. No. 10/681,018.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Mar. 1, 2016 for U.S. Appl. No. 14/087,930.
Notice of Allowance dated Mar. 21, 2012 for U.S. Appl. No. 12/487,864.

(56) References Cited

OTHER PUBLICATIONS

Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Notice of Allowance dated Apr. 15, 2011 for U.S. Appl. No. 12/487,868.
Notice of allowance dated Apr. 22, 2016 for U.S. Appl. No. 14/528,715.
Notice of Allowance dated Apr. 29, 2011 for U.S. Appl. No. 12/046,402.
Notice of Allowance dated May 23, 2011 for U.S. Appl. No. 09/990,909.
Notice of Allowance dated May 29, 2013 for U.S. Appl. No. 13/481,087.
Notice of allowance dated Jun. 12, 2014 for U.S. Appl. No. 13/448,061.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 9, 2015 for U.S. Appl. No. 13/193,346.
Notice of allowance dated Sep. 15, 2014 for U.S. Appl. No. 14/037,652.
Notice of Allowance dated Sep. 20, 2011 for U.S. Appl. No. 12/283,090.
Notice of allowance dated Oct. 29, 2013 for U.S. Appl. No. 13/204,881.
Notice of allowance dated Nov. 16, 2015 for U.S. Appl. No. 14/493,734.
Notice of allowance dated Dec. 23, 2014 for U.S. Appl. No. 14/007,793.
Notice of allowance dated Dec. 23, 2015 for U.S. Appl. No. 12/493,122.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
O'Connell. Hypertension Guide. cmbi.bjmu.edu. Jul. 14, 2008.
Office action dated Jan. 12, 2012 for U.S. Appl. No. 12/047,818.
Office action dated Jan. 15, 2014 for U.S. Appl. No. 13/836,135.
Office action dated Jan. 15, 2016 for U.S. Appl. No. 13/502,989.
Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Jan. 26, 2016 for U.S. Appl. No. 12/054,343.
Office action dated Jan. 29, 2016 for U.S. Appl. No. 12/786,739.
Office Action dated Feb. 1, 2012 for U.S. Appl. No. 12/493,122.
Office action dated Feb. 1, 2016 for U.S. Appl. No. 13/503,844.
Office action dated Feb. 14, 2013 for U.S. Appl. No. 13/193,346.
Office action dated Feb. 14, 2013 for U.S. Appl. No. 13/407,408.
Office action dated Feb. 17, 2016 for U.S. Appl. No. 14/713,178.
Office action dated Feb. 21, 2013 for U.S. Appl. No. 12/047,818.
Office action dated Feb. 26, 2016 for U.S. Appl. No. 12/535,676.
Office action dated Mar. 2, 2016 for U.S. Appl. No. 14/693,711.
Office Action dated Mar. 5, 2012 for U.S. Appl. No. 12/535,676.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office Action dated Mar. 19, 2012 for U.S. Appl. No. 13/204,881.
Office action dated Mar. 22, 2016 for U.S. Appl. No. 13/733,873.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office action dated Mar. 30, 2016 for U.S. Appl. No. 14/296,091.
Office action dated Apr. 4, 2016 for U.S. Appl. No. 13/313,629.
Office Action dated Apr. 5, 2012 for U.S. Appl. No. 11/555,697.
Office action dated Apr. 5, 2016 for U.S. Appl. No. 14/713,242.
Office action dated Apr. 6, 2015 for U.S. Appl. No. 14/493,734.
Office action dated Apr. 6, 2016 for U.S. Appl. No. 13/313,708.
Office Action dated Apr. 9, 2012 for U.S. Appl. No. 13/208,963.
Office action dated Apr. 10, 2014 for U.S. Appl. No. 13/502,989.
Office action dated Apr. 13, 2016 for U.S. Appl. No. 14/612,604.
Office action dated Apr. 16, 2014 for U.S. Appl. No. 13/705,763.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office Action dated Apr. 27, 2011 for U.S. Appl. No. 10/681,018.
Office action dated Apr. 27, 2015 for U.S. Appl. No. 12/054,343.
Office Action dated Apr. 28, 2011 for U.S. Appl. No. 12/283,090.
Office action dated May 6, 2015 for U.S. Appl. No. 12/493,122.
Office action dated May 7, 2015 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office Action dated May 24, 2011 for U.S. Appl. No. 12/487,864.
Office action dated May 27, 2015 for U.S. Appl. No. 13/502,989.
Office action dated Jun. 3, 2015 for U.S. Appl. No. 13/002,136.
Office action dated Jun. 13, 2012 for U.S. Appl. No. 12/493,122.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2012 for U.S. Appl. No. 12/493,147.
Office action dated Jun. 27, 2014 for U.S. Appl. No. 14/007,793.
Office action dated Jun. 29, 2011 for U.S. Appl. No. 11/555,697.
Office action dated Jul. 7, 2014 for U.S. Appl. No. 12/535,676.
Office action dated Jul. 11, 2012 for U.S. Appl. No. 12/573,353.
Office action dated Jul. 15, 2013 for U.S. Appl. No. 13/002,136.
Office action dated Jul. 18, 2012 for U.S. Appl. No. 12/047,818.
Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 13, 2012 for U.S. Appl. No. 13/208,963.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Aug. 31, 2015 for U.S. Appl. No. 12/535,676.
Office action dated Sep. 8, 2015 for U.S. Appl. No. 11/533,818.
Office action dated Sep. 9, 2013 for U.S. Appl. No. 13/502,989.
Office action dated Sep. 10, 2015 for U.S. Appl. No. 13/313,629.
Office action dated Sep. 11, 2015 for U.S. Appl. No. 13/313,708.
Office action dated Sep. 13, 2012 for U.S. Appl. No. 13/481,087.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.

(56) References Cited

OTHER PUBLICATIONS

Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 24, 2013 for U.S. Appl. No. 13/313,708.
Office action dated Oct. 25, 2012 for U.S. Appl. No. 13/144,286.
Office action dated Oct. 25, 2012 for U.S. Appl. No. 13/144,290.
Office action dated Oct. 30, 2015 for U.S. Appl. No. 14/528,715.
Office Action dated Oct. 5, 2010 for U.S. Appl. No. 12/046,402.
Office action dated Nov. 7, 2014 for U.S. Appl. No. 13/705,763.
Office Action dated Nov. 14, 2007 for U.S. Appl. No. 11/213,255.
Office Action dated Nov. 15, 2010 for U.S. Appl. No. 12/238,415.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Nov. 21, 2014 for U.S. Appl. No. 13/926,822.
Office Action dated Nov. 25, 2009 for U.S. Appl. No. 11/232,180.
Office Action dated Nov. 26, 2001 for U.S. Appl. No. 09/466,559.
Office action dated Nov. 29, 2013 for U.S. Appl. No. 13/193,346.
Office action dated Dec. 6, 2012 for U.S. Appl. No. 13/002,136.
Office action dated Dec. 10, 2013 for U.S. Appl. No. 13/407,408.
Office action dated Dec. 10, 2015 for U.S. Appl. No. 13/836,135.
Office Action dated Jan. 21, 2011 for U.S. Appl. No. 12/386,051.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 15, 2011 for U.S. Appl. No. 12/493,147.
Office action dated Dec. 15, 2015 for U.S. Appl. No. 14/087,930.
Office action dated Dec. 16, 2013 for U.S. Appl. No. 12/535,676.
Office action dated Dec. 18, 2014 for U.S. Appl. No. 14/037,696.
Office action dated Dec. 18, 2015 for U.S. Appl. No. 14/640,385.
Office Action dated Dec. 19, 2005 for U.S. Appl. No. 10/730,567.
Office action dated Dec. 19, 2014 for U.S. Appl. No. 13/733,873.
Office Action dated Dec. 22, 2006 for U.S. Appl. No. 10/681,018.
Office action dated Dec. 24, 2015 for U.S. Appl. No. 13/757,412.
Office Action dated Jan. 29, 2002 for U.S. Appl. No. 09/707,395.
Office Action dated Jan. 8, 2010 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Office action dated Jul. 17, 2015 for U.S. Appl. No. 13/733,873.
Office Action dated May 11, 2016 U.S. Appl. No. 14/713,242.

Okahata, et al. Lipid-coated enzymes as efficient catalysts in organic media. Trends in Biotechnology. 1997; 15(2):50-54.
Olivar-Parra, et al. Training referential communicative skills to individuals with autism spectrum disorder: a pilot study. Psychological Reports. 2011; 109:921-939.
Owley, et al. Multisite, double-blind, placebo-controlled trial of porcine secretin in autism. J Am Acad Child Adolesc Psychiatry. Nov. 2001;40(11):1293-9.
Pancrease. Patient information leaflet. Pancrease HL Capsules. Last updated Apr. 30, 2013. Janssen-cilag Ltd. www.medicines.org.uk/EMC/medicine/7326.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Pancreatin 8X USP Powder. Product Specification. Jul. 2000. In: Product Manual. American Laboratories Incorporated. Omaha, NE. p. 1.
Parisi et al. Evaluation of new rapid commercial enzyme immunoassay for detection of crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Patel, et al. Formulation and evaluation of mucoadhesive glipizide microspheres. AAPS PharmSciTech. 2005; 6(1):E49-E55.
PDTALKS. Motivational & Inspirational Speaking From a Parkinson's Patient Perspective. pdtalks.com/Parkinson_s_Disease.html. Jul. 14, 2008.
Perman et al. Role of ph in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Petrolatum: Pharmaceutical Excipients. London: Pharmaceutical Press. 2006. 1-6.
Pisani, et al. Levodopa-induced dyskinesia and striatal signaling pathways. Proc Natl Acad Sci USA. Mar. 3, 2009;106(9):2973-4. Epub Feb. 26, 2009.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatisis and pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.

(56) References Cited

OTHER PUBLICATIONS

Reeves, G. et al. Pharmacological Management of Attention-deficit hyperactivity disorder, Expert Opinion on Pharmacotherapy, 5:6; 1313-1320. (Feb. 25, 2005)DOI: 10.1517/14656566.5.6.1313 http://dx.doi.org/10.1517/14656566.5.6.1313.
Regan, et al. Comparative effects of antacids, cimetidine and enteric coating on the therapeutic response to oral enzymes in severe pancreatic insufficiency. N Engl J Med. Oct. 20, 1977;297(16):854-8.
Remtulla et al. Stool chymotrypsin activity measured by a spectrophotometric procedure to identify pancreat disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated May 22, 2007 for U.S. Appl. No. 11/213,255.
Restriction Requirement dated Sep. 12, 2006 for U.S. Appl. No. 10/681,018.
Revolution health. Enzyme therapy. revolutionhealth.com/drugs-treatments/enzyme-therapy. Sep. 2, 2008.
Richards, et al. Diagnosis, management, and treatment of Alzheimer disease: a guide for the internist. Arch Intern Med. Apr. 26, 1999;159(8):789-98.
Rider, et al. Perspective of biochemical research in the neuronal ceroid-lipofuscinosis. Am J Med Genet. Feb. 15, 1992;42(4):519-24.
Riedel, L et al. Limitations of faecal chymotrypsin as a screening test for chronic pancreatitis. Gut, 32:321-324 (1991).
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Roxas, et al. Colds and influenza: a review of diagnosis and conventional, botanical, and nutritional considerations. Alternative Medicine Review. 2007; 12(1):25-48.
Rubenstein, et al. Model of autism: increased ratio of excitation/inhibition in key neural systems. Genes Brain Behav. Oct. 2003;2(5):255-67.
Rudell, et al. The anterior piriform cortex is sufficient for detecting depletion of an indispensable amino acid, showing independent cortical sensory function. J Neurosci. Feb. 2, 2011;31(5):1583-90. Abstract only.
Sabra, et al. Linkage of ileal-lymphoid-nodular hyperplasia (ILNH), food allergy and CNS developmental: evidence for a non-IgE association. Ann Aller Asth Immunol. 1999; 82(1):81. Abstract only.
Sahelian. Enzymes. raysahelian.com/enzymes.html. Sep. 2, 2008.
Sandler, et al. Lack of benefit of a single dose of synthetic human secretin in the treatment of autism and pervasive developmental disorder. N Engl J Med. Dec. 9, 1999;341(24):1801-6.
Sandler et al. Short term benefit from oral vancomycin treatment of regressive-onset autism. J of Child Neuro. 2000; 15(7):42-435.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.
Schizophreniform disorder. Merck Manuals Online Medical Library. Nov. 2005. (in Japanese with English translation).
Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influecing food selectivity for children with autism spectrum disorders. Res Develop Disabil. 2006; 27:353-363.
Schumann. Medical, nutritional and technological properties of lactulose. An update. Eur J Nutr. Nov. 2002;41 Suppl 1:117-25.
Seltzer, et al. The Symptoms of Autism Spectrum Disorders in Adolescence and Adulthood. Journal of Autism and Developmental Disorders. 2003; 33(6):565-581.
Seneca et al. Enhancement of brain I-dopa concetration with a-chymotrypsm. J American Geriatrics Society. 1973; 256-258. Abstract only.
Serna, et al. Pathogenesis and treatment of Shiga toxin-producing *Escherichia coli* infections. Curr Opin Gastroenterol. Jan. 2008;24(1):38-47.
Settembre, et al. A block of autophagy in lysosomal storage disorders. Hum Mol Genet. Jan. 1, 2008;17(1):119-29.
Shadel. Expression and maintenance of mitochondrial DNA new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Shelby, et al. Enzymatic debridement with activated whole pancreas. American Journal of Surgery. Oct. 1958; 96(4):545-549.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Sillanaukee, et al. Improved diagnostic classification of alcohol abusers by combining carbohydrate-deficient transferrin and gamma-glutamyltransferase. Clin Chem. Apr. 2001;47(4):681-5.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh, et al. Plasma increase of interleukin-12 and interferon-gamma. Pathological significance in autism. J Neuroimmunol. May 1996;66(1-2):143-5.

(56) References Cited

OTHER PUBLICATIONS

Skeels et al. Crytosporidium infection in Oregon public health clinic patients 1985-88: the value of statewide laboratory surveillance. AJPH. 1990; 80(3):305-308.
Skinner, et al. Treatment of Prion Disease with Heterologous Prion Proteins. PLoS One. Jul. 2, 2015;10(7):e0131993. doi: 10.1371/journal.pone.0131993. eCollection 2015.
Smith, et al. Fecal chymotrypsin and trypsin determinations. Canadian Medical Association Journal. 1971; 104(8):691-4 and 697.
Sousa, et al. Polymorphisms in leucine-rich repeat genes are associated with autism spectrum disorder susceptibility in populations of European ancestry. Mol Autism. Mar. 25, 2010;1(1):7.
Statemaster. Number of Children with Autism (most recent) by state. Statemaster.com Jul. 14, 2008.
Statemaster. Number of Children with Autism (most recent w/graph) by state. Statemaster.com Jul. 14, 2003.
Statemaster. Number of Children with Autism (per capita)(most recent) by state. Statemaster.com Jul. 14, 2003.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Structural basis of 5-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Sundstrom, et al. A deadly prion disease: fatal familial insomnia. J Neurosci Nurs. Dec. 2003;35(6):300-5. Abstract only.
Supplemental Amendment and Response dated Jun. 8, 2010 to Restriction Requirement dated Oct. 7, 2009 for U.S. Appl. No. 12/283,090.
Swayne, et al. Pathobiology of H5N2 Mexican avian influenza virus infections of chickens. Vet Pathol. Nov. 1997;34(6):557-67.
Tager-Flusberg, et al. Language disorders: autism and other pervasive developmental disorders. Pediatr Clin North Am. Jun. 2007;54(3):469-81, vi.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
Terrie, et al. Understanding Pancreatic Enzyme Products. Dec. 15, 2008.
The Alzheimer's Association. Basics of Alzheimers Disease. 2005, 32 pages. http://www.alz.org/national/documents/brochure_Basicsofalz_low/pdf.
Thefreedictionary. Term Sprinkles. Www.thefreedictionary.com. Accessed Nov. 2, 2011. 1 page.
Therapeutic research center. Approved Pancreatic Enzyme Products. Pharmacist's Letter/Prescribers Letter 2010. Oct. 2010. 1-3.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Tran, et al. Treatment of complex regional pain syndrome: a review of the evidence. Can J Anaesth. Feb. 2010;57(2):149-66.
Trauner, et al. Specific cognitive deficits in young children with cystinosis: evidence for an early effect of the cystinosin gene on neural function. J Pediatr. Aug. 2007;151(2):192-6.
Troy. Pancreatic Enzymes. Remington: The Science and Practice of Pharmacy, 21st edition. Lippincot Williams & Wilkins, 2006. p. 1304.
Tsan, et al. Heat shock proteins and immune system. J Leukoc Biol. Jun. 2009;85(6):905-10.
Tsang et al. Extragastroduodenal conditions associated with Heliobacter pylori infection. Hong Kong Medical Journal. 1999; 5(2):169-174.
Uhlmann, et al. Potential viral pathogenic mechanism for new variant inflammatory bowel disease. Mol Pathol. Apr. 2002;55(2):84-90.
ULTRESA—FDA Prescribing Information Side Effects and Uses. Revised Sep. 2014.
ULTRESA. Highlights of prescribing information. Aptalis Pharma US Inc. Revised Mar. 2012.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif. students triples. United Press International. Jul. 12, 2008.
U.S. Appl. No. 11/533,818 Final Office Action dated Jun. 7, 2016.
U.S. Appl. No. 12/054,343 Office Action dated Aug. 19, 2016.
U.S. Appl. No. 12/535,676 Non-Final Office Action dated Apr. 21, 2017.
U.S. Appl. No. 12/535,676 Office Action dated Sep. 13, 2016.
U.S. Appl. No. 12/786,739 Office Action dated Sep. 20, 2016.
U.S. Appl. No. 13/002,136 Final Office Action dated Jun. 24, 2016.
U.S. Appl. No. 13/002,136 Non-Final Office Action dated Feb. 27, 2017.
U.S. Appl. No. 13/193,346 Notice of Allowability dated Jul. 14, 2016.
U.S. Appl. No. 13/193,346 Notice of Allowability dated Jun. 2, 2016.
U.S. Appl. No. 13/313,629 Notice of Allowance dated Dec. 22, 2016.
U.S. Appl. No. 13/313,708 Notice of Allowance dated Dec. 15, 2016.
U.S. Appl. No. 13/502,989 Notice of Allowance dated Aug. 10, 2016.
U.S. Appl. No. 13/503,844 Office Action dated Aug. 25, 2016.
U.S. Appl. No. 13/503,844 Office Action dated Mar. 27, 2017.
U.S. Appl. No. 13/705,763 Final Office Action dated May 24, 2016.
U.S. Appl. No. 13/757,412 Final Office Action dated Jun. 30, 2016.
U.S. Appl. No. 13/757,412 Office Action dated Feb. 10, 2017.
U.S. Appl. No. 13/836,135 Office Action dated Jul. 22, 2016.
U.S. Appl. No. 14/296,091 Final Office Action dated Jan. 3, 2017.
U.S. Appl. No. 14/612,580 Office Action dated Sep. 21, 2016.
U.S. Appl. No. 14/612,604 Notice of Allowance dated Jul. 20, 2016.
U.S. Appl. No. 14/639,425 Notice of Allowance dated Mar. 10, 2017.
U.S. Appl. No. 14/639,425 Office Action dated Jul. 14, 2016.
U.S. Appl. No. 14/640,385 Supplemental Notice of Allowability dated May 26, 2016.
U.S. Appl. No. 14/693,711 Final Office Action dated Dec. 15, 2016.
U.S. Appl. No. 14/693,711 Notice of Allowance dated Apr. 21, 2017.
U.S. Appl. No. 14/713,178 Advisory Office Action dated Jan. 19, 2017.
U.S. Appl. No. 14/713,178 Final Office Action dated Oct. 14, 2016.
U.S. Appl. No. 14/713,178 Notice of Allowance dated Apr. 12, 2017.
U.S. Appl. No. 14/713,221 Final Office Action dated Jun. 16, 2016.
U.S. Appl. No. 14/713,221 Non-Final Office Action dated Dec. 30, 2016.
U.S. Appl. No. 14/713,242 Office Action dated Dec. 7, 2016.
U.S. Appl. No. 14/921,896 Office Action dated Apr. 26, 2017.

(56) References Cited

OTHER PUBLICATIONS

U.S. Appl. No. 15/074,115, filed Mar. 18, 2016.
U.S. Appl. No. 15/089,842, filed Apr. 4, 2016.
U.S. Appl. No. 14/528,715, filed Oct. 30, 2014.
U.S. Appl. No. 14/612,580, filed Feb. 3, 2015.
U.S. Appl. No. 14/612,604, filed Feb. 3, 2015.
U.S. Appl. No. 14/639,425, filed Mar. 5, 2015.
U.S. Appl. No. 14/640,385, filed Mar. 6, 2015.
U.S. Appl. No. 14/693,711, filed Apr. 22, 2015.
U.S. Appl. No. 14/713,178, filed May 15, 2015.
U.S. Appl. No. 14/713,221, filed May 15, 2015.
U.S. Appl. No. 14/71,3242, filed May 15, 2015.
U.S. Appl. No. 14/612,580 Office Action dated Dec. 24, 2015.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
USP (32)-NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
VIOKACE—FDA Prescribing Information, Side Effects and Uses. Revised Mar. 2012.
VIOKACE. Highlights of prescribing information. Aptalis Pharma US Inc. Revised Mar. 2012.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Clinical Perspectives in Autism. 2002; 74-81.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004; 82:835-839.
Wang, et al. Activation of Ras/Erk pathway by a novel MET-interacting protein RanBPM. J Biol Chem. Sep. 27, 2002;277(39):36216-22.
Wang, et al. Effect of chymotrypsin C and related proteins on pancreatic cancer cell migration. Acta Biochim Biophys Sin (Shanghai). May 2011;43(5):362-71. Epub Apr. 2, 2011. Jan. 7, 2011. Abstract only.
We Move, PD Workbook, The WEMOVE Clinician's Guide to Parkinson's Disease, 2006.
Weintraub, et al. Morphometric studies of pancreatic acinar granule formation in NCTR-Balb/c mice. J Cell Sci. May 1992;102 ( Pt 1):141-7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Williams, et al. Intravenous secretin for autism spectrum disorders (ASD). Cochrane Database Syst Rev. Apr. 18, 2012;4:CD003495. doi: 10.1002/14651858.CD003495.pub3.
Wisniewski, et al. Therapeutic approaches for prion and Alzheimer's diseases. FEBS J. Aug. 2007;274(15):3784-98. Epub Jul. 6, 2007.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous sesions and inflammatory fluids. Cellular and Molecular Life Sciences. 1969; 25(9):953-954.
Wolfson, D., Making sense of digestive enzymes, Klaire Labs, Mar. 13, 2006.
Woodward et al. Ischaemic enterocolitis complicating aidiopathic dysatuonomia. Gut. 1998; 43:285-287.
Xu. Pancreatin therapy in chronic pancreatitis. Clin J Dig, May 2005; 25(5):313-315. (in Chinese with English translation).
Yahoo!.com. Who is affected by Parkinson's disease. Yahoo! Health. Jul. 14, 2008.
Yang, et al. Polymeric Porous Framework of a Bismuth Citrate-Based Complex: A Potential Vehicle for Drug Delivery. Medical News Today. Dec. 17, 2010. 1-4.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
ZENPEP—FDA Prescribing Information, Side Effects and Uses. Revised Sep. 2014.
ZENPEP. Highlights of prescribing information. Eurand Pharmaceuticals Inc. Revised Jul. 2011.
Zhang et al. Lactulose-mannitol intestinal permeability test in children with diarrhea caused by rotavirus and cryptosporidium. J of Pediatric Gastro & Nutrition. 2000; 31(1):16-21.
Alexrod FB et al. Hereditary sensory an autonomic neuropathies: types II, III and IV. Orphanet Journal of Rare Diseases, 2:39 (2007).

(56) References Cited

OTHER PUBLICATIONS

Anderson, George M., et al. Determination of serotonin in whole blood, platelet-rich plasma, platelet-poor plasma and plasma ultrafiltrate. Life Sciences 40(11):1063-1070 (Mar. 16, 1987) [Abstract Only].
Arnold, GL et al. Plasma amino acids profiles in children with autism: potential risk of nutritional deficiencies. J. Autism Dev. Disord. 33(4):449-454 (Aug. 2003) [Abstract Only].
Balasubramanian, Mukundh N. et al. Asparagine synthetase: regulation by cell stress and involvement in tumor biology, Am. J. Physiol. Endocrinol. Metab. 304(8):E789-E799 (Apr. 15, 2013).
Beliaev, O.A. The therapeutic efficacy of the triase preparation in experimental pancreatic exocrine insufficiency. Eksp Lin Farmakiol. 57:38-40 (1994) (Abstract Only—English Translation).
Chen, Li et al. Antibiotic effect of lysostaphin on granulation wound. Acta Academiae Medicinae Militaris Tertiae, 8(14) p. 1 Abstract (2006).
Co-pending U.S. Appl. No. 15/840,883, filed Dec. 13, 2017.
Co-pending U.S. Appl. No. 16/010,850, filed Jun. 18, 2018.
Co-pending U.S. Appl. No. 16/103,192, filed Aug. 14, 2018.
Coutinho, AM et al. Variants of the serotonin transporter gene (SLC6A4) significantly contribute to hyperserotonemia in autism. Mol Psychiatry. Mar. 2004;9(3):264-71.
Fafournoux, P. et al. Amino acid regulation of gene expression. Biochemical Journal, 351:1-12(2000).
Girella, E. et al. The assay of chymotrypsin in stool as a simple and effective test of exocrine pancreatic activity in cystic fibrosis. Pancreas, 3(3):254-262 (1988).
International Application No. PCT/US18/26841 International Search Report and Written Opinion dated Jul. 3, 2018.
Nestler, et al. Delta-FosB: A sustained molecular switch for addiction. PNAS 98(20): 11042-11046 (Sep. 25, 2001).
O'Keefe, Stephen J.D. et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Felig, P. Amino acid metabolism in man. Annual Review of Biochemistry, 44(1):933-955 (1975). [Abstract Only].
Chez, M. et al. Secretin and autism: A two-part clinical investigation. Journal of Autism and Developmental Disorders, 30(2), 87-94 (Apr. 2000) [Abstract Only].
Evans, C. et al. Altered amino acid excretion in children with autism. Nutritional Neuroscience, 11(1):9-17 (Feb. 2008).
First, M.Structured clinical interview for DSM-IV-TR axis I disorders, research version, patient edition. (SCID-I/P) New York: Biometrics Research, New York State Psychiatric Institute. (2002).
Guesnet, P. et al. Docosahexaenoic acid (DHA) and the developing central nervous system (CNS)—Implications for dietary recommendations. Biochimie, 93(1):7-12(2011). [Abstract Only].
Heil, M., et al. Low endogenous fecal chymotrypsin: a possible biomarker for autism. Poster presented at the annual IMFAR Conference on Autism, Atlanta, GA.(May 2014) p. 1.
Matthews, D. Intestinal absorption of amino acids and peptides. Proceedings of the Nutrition Society, 31(2):171-177(1972).
McClung, C.A. et al. DeltaFosB: A molecular switch for long-term adaptation in the brain. Molecular Brain Research, 132(2):146-154 (Dec. 20, 2004).
Morimoto, R. The heat shock response: Systems biology of proteotoxic stress in aging and disease. Cold Spring Harbor Symposia on Quantitative Biology, 76:91-99 (2011) (Epub: Feb. 27, 2012).
Munasinghe, S.A. et al. Digestive enzyme supplementation for autism spectrum disorders: A double-blind randomized controlled trial. Journal of Autism and Developmental Disorders, 40(9):1131-1138 (Sep. 2010) [Abstract Only].
Naushad, Shaik Mohammad et al. Autistic children exhibit distinct plasma amino acid profile. Indian Journal of Biochemistry and Biophysics, 50(5):474-478 (Oct. 2013).
Patton, J. et al. Factor structure of the barratt impulsiveness scale. Journal of Clinical Psychology, 51(6): 768-774 (Nov. 1995).
Robinson, T. et al. Incentive-sensitization and addiction. Addiction, 96(1):103-114 (Jan. 2001).
Schedl, H. et al. Absorption of l-methionine from the human small intestine. Journal of Clinical Investigation, 47(2): 417-425 (1968).
Rivest, J. et al. A dynamic model of protein digestion in the small intestine of pigs. Journal of Animal Science, 78(2):328-240 (Feb. 2000).
Avruch, J., et al. Amino acid regulation of TOR complex 1. AJP: Endocrinology and Metabolism, Am. J. Physiol. Endocrinol. Metab. 296(4):E592-E602 (Apr. 2009).
Daly, E., et al. Response inhibition and serotonin in autism: A functional MRI study using acute tryptophan depletion. Brain, 137(9), 2600-2610 (Sep. 2014).
Drabkin, H., et al. Initiation of protein synthesis in mammalian cells with codons other than AUG and amino acids other than methionine. Molecular and Cellular Biology, 18(9): 5140-5147 (Sep. 1998).
Fairclough, P. et al. Comparison of the absorption of two protein hydrolysates and their effects on water and electrolyte movements in the human jejunum. Gut, 21(10):829-834 (1980).
McClung, C., et al. Regulation of gene expression and cocaine reward by CREB and DeltaFosB. Nature Neuroscience, 6(11):1208-1215 (2003). [Abstract Only].
Nestler, E.J. Molecular basis of long-term plasticity underlying addiction. Nature Reviews Neuroscience, 2(2):119-128 (Feb. 2001).
Norton, L. et al. Leucine regulates translation initiation of protein synthesis in skeletal muscle after exercise. The Journal of Nutrition, 136(2):533S-537S (Feb. 2006).
Schain, RJ et al. Studies on 5-hydroxyindole metabolism in autistic and other mentally retarded children. J. Pediatr. 58:315-320 (1961) [Summary Only].
Tang, G. et al. Loss of mTOR-dependent macroautophagy causes autistic-like synaptic pruning deficits. Neuron, 83(5):1131-1143 (Sep. 3, 2014).
Williams, K. et al. Cochrane Review: Selective serotonin reuptake inhibitors (SSRIs) for autism spectrum disorders (ASD). Evidence-Based Child Health: A Cochrane Review Journal, 6(4):1044-1078 (Jul. 2011). [Abstract Only].
U.S. Appl. No. 12/054,343 Non-Final Office Action dated Dec. 26, 2017.
U.S. Appl. No. 12/786,739 Non-Final Office Action dated Jan. 4, 2018.
U.S. Appl. No. 13/002,136 Advisory Office Action dated Jul. 9, 2018.
U.S. Appl. No. 13/002,136 Final Office Action dated Jan. 8, 2018.
U.S. Appl. No. 13/733,873 Final Office Action dated Feb. 21, 2018.
U.S. Appl. No. 13/836,135 Non-Final Office Action dated Mar. 15, 2018.
U.S. Appl. No. 14/296,091 Non-Final Office Action dated Mar. 22, 2018.
U.S. Appl. No. 14/612,580 Notice of Allowability dated Mar. 1, 2018.
U.S. Appl. No. 14/612,580 Notice of Allowance dated Jan. 12, 2018.
U.S. Appl. No. 14/713,242 Non-Final Office Action dated Mar. 29, 2018.
U.S. Appl. No. 14/921,896 Final Office Action dated Jan. 25, 2018.
U.S. Appl. No. 14/921,896 Notice of Allowance dated Jul. 18, 2018.
U.S. Appl. No. 15/089,842 Non-Final Office Action dated Jun. 26, 2018.
U.S. Appl. No. 15/164,493 Non-Final Office Action dated Feb. 27, 2018.
U.S. Appl. No. 15/265,415 Non-Final Office Action dated Apr. 11, 2018.
U.S. Appl. No. 15/265,620 Non-Final Office Action dated Jun. 20, 2018.
Yang, Xinyi et al. Advances in anti-staphylococcal agent lysostaphin. Chinese Journal of New Drugs 14(9):1113-1117 (2005).

* cited by examiner

PHARMACEUTICAL PREPARATION FOR THE TREATMENT OF THE SYMPTOMS OF ADDICTION AND METHOD OF DIAGNOSING SAME

RELATED APPLICATIONS

This application is a continuation of U.S. application Ser. No. 14/639,425, filed Mar. 5, 2015, now U.S. Pat. No. 9,687,534, issued on Jun. 27, 2017, which is a continuation of U.S. application Ser. No. 13/926,822, filed Jun. 25, 2013, now U.S. Pat. No. 9,017,665, issued on Apr. 28, 2015, which is a continuation of U.S. application Ser. No. 13/562,999, filed Jul. 31, 2012, now U.S. Pat. No. 8,486,390, issued on Jul. 16, 2013, which is a continuation of U.S. application Ser. No. 13/271,783, filed Oct. 12, 2011, now U.S. Pat. No. 8,318,158, issued on Nov. 27, 2012, which is a continuation of U.S. application Ser. No. 12/426,794, filed Apr. 20, 2009, now U.S. Pat. No. 8,084,025, issued on Dec. 27, 2011, which claims the benefit of U.S. Provisional Patent Application No. 61/046,026 filed on Apr. 18, 2008, each of which is incorporated by reference herein in its entirety.

TECHNICAL FIELD

The invention relates to a treatment for the symptoms of addiction, and more particularly, to the use of digestive/pancreatic enzymes in the treatment of the symptoms of drug and alcohol addiction. The invention further relates to method of diagnosing the symptoms of addiction. More particularly, the invention further relates to measuring fecal chymotrypsin levels to diagnose the symptoms of drug and alcohol addiction and the possibility of relapse into drug and alcohol addiction.

BACKGROUND OF THE DISCLOSURE

Addiction is a dependence on a behavior or substance that a person is powerless to stop. The term has been partially replaced by the word "dependence" for substance abuse. Addiction has been extended, however, to include mood-altering behaviors or activities. Some researchers speak of two types of addictions: substance addictions (for example, alcoholism, drug abuse, and smoking); and process addictions (for example, gambling, spending, shopping, eating, and sexual activity). There is a growing recognition that many addicts, such as polydrug abusers, are addicted to more than one sub-stance or process.

Addiction is one of the most costly public health problems in the United States. It is a progressive syndrome, which means that it increases in severity over time unless it is treated. Substance abuse is characterized by frequent relapse, or return to the abused substance. Substance abusers often make repeated attempts to quit before they are successful.

In 1995, the economic cost of substance abuse in the United States exceeded $414 billion, with health care costs attributed to substance abuse estimated at more than $114 billion.

By eighth grade, 52% of adolescents have consumed alcohol, 41% have smoked tobacco, and 20% have smoked marijuana. Compared to females, males are almost four times as likely to be heavy drinkers, nearly one and a half more likely to smoke a pack or more of cigarettes daily, and twice as likely to smoke marijuana weekly. However, among adolescents these gender differences are decreasing. Although frequent use of tobacco, cocaine and heavy drinking appears to have remained stable in the 1990s, marijuana use increased.

In 1999, an estimated four million Americans over the age of 12 used prescription pain relievers, sedatives, and stimulants for "nonmedical" reasons during one month.

In the United States, 25% of the population regularly uses tobacco. Tobacco use reportedly kills 2 5 times as many people each year as alcohol and drug abuse combined. According to 1998 data from the World Health Organization, there were 1.1 billion smokers worldwide and 10,000 tobacco-related deaths per day. Furthermore, in the United States, 43% of children aged 2 to 11 years are exposed to environmental tobacco smoke, which has been implicated in sudden infant death syndrome, low birth weight, asthma, middle ear disease, pneumonia, cough, and upper respiratory infection.

Individuals going through alcohol rehabilitation or breaking drug addiction know the pain that chemicals can cause. All recovering alcoholics and drug users understand the toll that drug abuses take on the body, mind and emotions. Alcohol and drugs cause tremendous nutrient deficiencies as well as a need for very specific nutrients that are only found within nature's foods. These nutrients:

Support the liver
Help the body detoxify
Produce energy
Rebuild vitamin and mineral levels
Feed the brain and emotions
Support the blood vessels
Feed the nervous system
Balance blood sugar One of the most obvious signs of drug and alcohol abuse is the depletion of the vitamin B complex. The challenge of addiction recovery can be made more difficult when coupled with nutritional deficiencies. The chronic depletion of vitamin B complex, for example, can lead to adrenal depletion as well. Since vitamin B complex provides cellular energy, nervous transmission, muscle health (contraction and relaxation), heart health, blood sugar metabolism, normal weight control, cellular regrowth and many functions related to emotional stability and thinking processes, this vitamin complex is absolutely necessary for replenishment. But vitamin B complex should only come from food, not from isolated or groups of vitamin pills. Similarly, the depletion of minerals such as calcium is very serious. Other important minerals include selenium, phosphorus, sulfur, zinc, potassium, and magnesium, which are all found in nature's raw vegetables.

Of course, the liver is one of the most injured organs in cases of alcoholism and drug abuse. The reason is because the liver is part of the digestive system and is used by the body to filter out and store toxins. When it is overtaxed, the liver can become fatty or damaged or both. It is critical that those going through drug or alcohol rehabilitation emphasize liver healing.

Alcohol blocks the absorption and breakdown of nutrients by damaging the cells lining the stomach and intestines, and by decreasing the amount of digestive enzymes secreted by the pancreas. For reasons that aren't yet known, the pancreas can become inflamed and leak digestive enzymes, which then attack the pancreas itself. Pancreatitis is extremely painful and can be fatal.

In view of such findings, there is need for a method of treating those exhibiting symptoms of drug and alcohol addiction.

No description in the Background section should be taken as an admission that such disclosure constitutes prior art to the instant invention.

SUMMARY OF THE DISCLOSURE

The present invention is directed to the use of therapeutic agents in the treatment of the symptoms of drug and alcohol addiction and the method of preparing those agents. Further, the invention is directed to a method of diagnosing the symptoms of addiction and the possibility of relapse into drug and alcohol addiction.

More specifically, the present invention relates to stable pharmaceutical preparations containing, but not limited to, digestive/pancreatic enzymes, including, but not limited to, amylases, proteases, cellulase, papaya, papain, bromelain, lipases, chymotrypsin and hydrolases. This combination is made by, but not limited to: direct compression, microencapsulation, lipid encapsulation, wet granulation or other methods including the use of PROSOLV® microencapsulation, lipid encapsulation technology, or other suitable technology. This technology can include the use of rapid dissolution (rapid dissolve), time release or other delivery methods including oral, injection, patch or other method. Further, the delivery of the enzymes can be in the form of a tablet, sprinkles, sachet, capsules, caplets or other compressed tablet delivery, or other oral delivery method.

Further, the invention is directed toward the use of a biomarker, the presence of chymotrypsin in the GI tract to determine a lack of protein digestion, nutrient absorption, and other related symptoms of drug and alcohol addiction.

It is a goal of the present invention to provide therapeutic agents for the treatment of the symptoms of drug and alcohol addiction and provide a method for preparing those agents.

Another goal of the present invention is to formulate stable pharmaceutical preparations containing, but not limited to, digestive/pancreatic enzymes including, but not limited to, amylases, proteases, cellulase, papaya, papain, bromelain, lipases, chymotrypsin; and hydrolases.

Yet another goal of the present invention is to make a combination of digestive/pancreatic enzymes utilizing, by but not limited to: direct compression, microencapsulation, lipid encapsulation, wet granulation or other methods including the use of PROSOLV®, and other known excipients and additives to accomplish microencapsulation, lipid encapsulation, direct compression, wet or dry granulation or other suitable technology.

A further goal of the present invention is to deliver the preparation by means, which can include the use of rapid dissolution (rapid dissolve), time release, or other delivery methods including oral, injection, patch, or other method. Further, the delivery of the enzymes may be in the form of a tablet, capsule, sprinkles, sachet, or other oral delivery method.

An additional goal of the invention is to demonstrate the use of fecal chymotrypsin as a prognosticative indicator of the presence of the symptoms of drug and alcohol addiction, or the likelihood of an individual to relapse into drug and alcohol addiction.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

The individual who is diagnosed as alcoholic or as substance abuse addicted is administered a fecal chymotrypsin test where the level of the enzyme chymotrypsin is measured. The individual is then given an effective amount of pancreatic/digestive enzymes if the fecal chymotrypsin level is below 8.4 U/mg. This level is considered abnormal when compared to an individual without alcoholism or substance abuse addiction, or who is not at risk for such an addiction, or having been addicted at any time in the past, or who has other protein digestion problems.

The fecal chymotrypsin levels may be measured in someone at risk for becoming an alcoholic or substance abuse addicted or who has had a history of alcoholism or substance abuse and who may again become an alcoholic or substance abuse addicted. The steps involve the following: taking a stool sample from the individual to be diagnosed, measuring the level of fecal chymotrypsin in the stool sample, and comparing that level to an individual who does not have alcoholism, a substance abuse problem or other protein digestion problem. When the level is low, less than 8.4 U/mg, an effective amount of pancreatic enzymes is administered to the individual.

The invention may be used as the or one of the components of an alcohol treatment or substance abuse treatment program for an active alcoholic or substance abuse addict. The invention may also be utilized to keep someone at risk for becoming an alcoholic or substance abuser or it may be used to prevent someone from relapse into addiction. The pancreatic/digestive enzymes may be given to prevent addiction, such as alcoholism or substance abuse, to help someone who is presently an addict such as an alcoholic or drug addict, or to someone who is at risk of relapse. The enzymes may be administered as a result of a lowered fecal chymotrypsin level.

Pancreatic/digestive enzymes may be administered to those who are presently battling active addiction such as alcoholism or drug abuse. They may be given to those who are not actively addicted, but who have been addicted at another time and who are at risk for becoming an addict, such as an alcoholic, drug addict or other substance abuse addict. They may also be utilized for those who are deemed at risk for addiction, such as alcoholism, due to family history or other historical events, such as severe stress or other factors placing the individual at risk.

In one embodiment, a stable preparation of digestive/pancreatic enzymes is formed into a dosage formulation containing a therapeutically effective amount of a protease, an amylase, and/or a lipase. The formulation may include additional enzymes, such as pancreatin, chymotrypsin, trypsin, papain and/or papaya. Other combinations of digestive enzymes may also be used. These enzymes can be in the form of animal or plant derivatives, natural or synthetic.

The following outlines a formulary for digestive/pancreatic enzymes for treating the symptoms of addiction; Amylase 10,000-60,000 U.S.P.; Protease 10,000-70,000 U.S.P.; Lipase 4,000-30,000 U.S.P.; Pancreatin 2,000-6,000 U.S.P.; Chymotrypsin 2-5 mg; Trypsin 60-100 mg; Papain 3,000-10,000 U.S.P. units/mg; Papaya 30-60 mg.

The dosage formulation may be administered by an oral preparation including, but not limited to, an encapsulated tablet, a mini-tab, a microcapsule, a mini-capsule, a time released capsule, a sprinkle or other methodology. In one embodiment, the oral preparation is encapsulated using PROSOLV® technology. Alternatively, the oral preparation may be encapsulated using enteric coating, lipid encapsulation, direct compression, dry granulation, wet granulation, and/or a combination of these methods.

Fecal chymotrypsin is a sensitive, specific measure of proteolytic activity. Normal levels of chymotrypsin are considered be greater than 8.4 U/gram. Decreased values (less than 8.4 U/gram) suggest diminished pancreatic output (pancreatic insufficiency), hypoacidity of the stomach or cystic fibrosis. Elevated chymotrypsin values suggest rapid transit time, or less likely, a large output of chymotrypsin from the pancreas.

For the fecal chymotrypsin test, a stool sample is collected from each of the subjects. Each stool sample is analyzed using an enzymatic photo spectrometry analysis to determine the level of fecal chymotrypsin in the stool. Alternatively, other methods, such as the colorimetric method, use of substrates, use of assays, and/or any other suitable method may be used to measure the fecal chymotrypsin levels. The levels of fecal chymotrypsin in the samples of the individuals to be diagnosed are compared to the levels of fecal chymotrypsin in an individual who does not have alcoholism, a substance abuse problem or other protein digestion problem to determine if the individual being diagnosed would benefit from the administration of digestive enzymes.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for treating an individual addicted to cocaine and having a chymotrypsin deficiency, the method comprising administering to the individual a therapeutically effective amount of a pharmaceutical preparation that comprises digestive enzymes, whereby the cocaine addiction is treated.

2. The method of claim 1, wherein the digestive enzymes comprise an amylase, a lipase, and a protease.

3. The method of claim 1, wherein the digestive enzymes consist of an amylase, a lipase, and a protease.

4. The method of claim 1, wherein the digestive enzymes are selected from the group consisting of animal enzymes, plant enzymes, synthetic enzymes, and a combination thereof.

5. The method of claim 1, wherein the pharmaceutical preparation is administered orally via a dosage formulation selected from the group consisting of a pill, a tablet, a capsule, a microcapsule, a mini-capsule, a time released capsule, a mini-tab, a sprinkle, and a combination thereof.

6. The method of claim 2, wherein the digestive enzymes comprise the amylase, and wherein the amount of amylase in the pharmaceutical preparation ranges from 10,000 to 60,000 U.S.P. units/dose.

7. The method of claim 2, wherein the digestive enzymes comprise the protease, and wherein the amount of protease in the pharmaceutical preparation ranges from 10,000 to 70,000 U.S.P. units/dose.

8. The method of claim 2, wherein the digestive enzymes comprise the lipase, and wherein the amount of lipase in the pharmaceutical preparation ranges from 4,000 to 30,000 U.S.P. units/dose.

9. The method of claim 1, wherein determination that the individual has the chymotrypsin deficiency comprises measuring a level of chymotrypsin in a stool sample obtained from the individual with enzymatic photospectrometry or a colorimetric method, and comparing the level of chymotrypsin present in the stool sample to a normal level of chymotrypsin.

* * * * *